(12) United States Patent
Franchini et al.

(10) Patent No.: US 6,515,010 B1
(45) Date of Patent: Feb. 4, 2003

(54) CARVEDILOL METHANESULFONATE

(75) Inventors: Miriam Franchini, Allentown, NJ (US); Gopadi M. Venkatesh, Bell Brook, OH (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/149,501

(22) PCT Filed: Nov. 13, 2000

(86) PCT No.: PCT/US00/31056

§ 371 (c)(1), (2), (4) Date: May 15, 2002

(87) PCT Pub. No.: WO01/35958

PCT Pub. Date: May 25, 2001

Related U.S. Application Data

(60) Provisional application No. 60/165,545, filed on Nov. 15, 1999.

(51) Int. Cl.$^7$ .................. A61K 31/403; C07D 209/88
(52) U.S. Cl. .............. 514/411; 548/444; 424/448; 424/449; 424/457; 424/468; 424/474; 424/490
(58) Field of Search ................... 514/411; 548/444; 424/448, 449, 457, 468, 474, 490

(56) References Cited

U.S. PATENT DOCUMENTS

| 4,503,067 A | 3/1985 | Wiedemann et al. ....... 514/411 |
| 2002/0054911 A1 * | 5/2002 | Oh .............................. 424/488 |

* cited by examiner

*Primary Examiner*—Fiona T. Powers
(74) *Attorney, Agent, or Firm*—Mary E. McCarthy; Charles M. Kinzig

(57) ABSTRACT

This invention relates to carvedilol methanesulfonate, compositions containing this compound and methods of using carvedilol methanesulfonate to treat hypertension, congestive heart failure and angina.

8 Claims, No Drawings

CARVEDILOL METHANESULFONATE

This application claims the benefit of Provisional Application No. 60/165,545, filed Nov. 15, 1999.

FIELD OF THE INVENTION

This invention relates to a pharmaceutically active compound, compositions containing the compound and methods of using the compound in the treatment of certain disease states in mammals, in particular man. More specifically, the present invention relates to carvedilol methanesulfonate, which is the methanesulfonate salt of 1-(carbazol-4-yloxy-3-[[2-(o-methoxyphenoxy)ethyl]amino]-2-propanol, compositions containing this compound, and methods of using carvedilol methanesulfonate to treat hypertension, congestive heart failure and angina.

BACKGROUND OF THE INVENTION

U.S. Pat. No 4,503,067 describes a compound which is known as carvedilol. This compound is a novel multiple action drug useful in the treatment of hypertension and angina. Carvedilol is known to be both a competitive non-selective β-adrenoceptor antagonist and a vasodilator. The vasodilatory actions of carvedilol result primarily from $α_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug. Also, carvedilol, as a consequence of its antioxidant action in attenuating oxygen free radical-initiated lipid peroxidation, is useful in organ protection, in particular, cardioprotection. Additionally, carvedilol is useful in the treatment of congestive heart failure.

The currently marketed formulation of carvedilol is a conventional, swallow tablet and prescribed as a twice-a-day medication in the United States. This formulation is in immediate release form; that is to say the nature of the formulation is such that by the time carvedilol leaves the stomach, it is either in solution or it is in the form of a suspension of fine particles, i.e. a form from which carvedilol can be readily absorbed.

Carvedilol, a free base with one pKa of 7.6, exhibits a predictable solubility behavior in neutral or alkaline media, i.e. above pH 9.0, the solubility is relatively low (<1 ug/mL). The solubility increases with decreasing pH and eventually reaches a plateau with a broad peak (~0.2 mg/mL) at a pH of 4–5. At acidic pHs of 1 to 4 in buffers, the solubility is limited by the solubility of the protonated form of carvedilol or its salt formed in-situ. The hydrochloride salt form formed in-situ in an acidic medium, such as simulated gastric fluid, is less soluble in water than carvedilol itself.

Surprisingly, it has been found that unlike carvedilol or certain salt forms of carvedilol, carvedilol methanesulfonate exhibits a solubility of >8.0 mg/ml in purified water at 25° C. Thus, carvedilol methanesulfonate may result in a dosage form from which the drug substance becomes available for bioabsorption throughout the gastrointestinal tract. Hence, it may be possible to develop controlled release once-a-day (uid) and twice-a-day (bid) dosage forms, delayed release or pulsatile release dosage forms. Also, carvedilol methanesulfonate may be formulated in an injectible form or as a transdermal patch. The high solubility feature of carvedilol methanesulfonate is particularly important when formulating this compound for therapeutic use.

SUMMARY OF THE INVENTION

The present invention provides a novel salt form of carvedilol, namely carvedilol methanesulfonate.

The present invention also provides pharmaceutical compositions containing carvedilol methanesulfonate and the use of this compound in the treatment of hypertension, congestive heart failure and angina.

DETAILED DESCRIPTION OF THE INVENTION 1-(Carbazol-4-yloxy-3-[[2-(o-methoxyphenoxy)ethyl]amino]-2-propanol is known as carvedilol. This compound has the following structure:

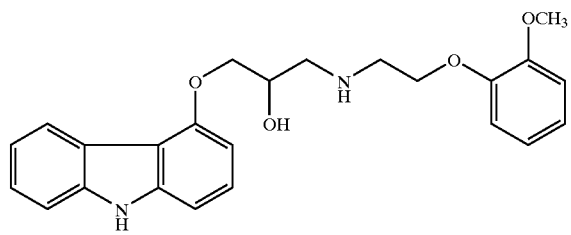

and is claimed in U.S. Pat. No. 4,503,067 (assigned to Boehringer Mannheim, GmbH, Mannheim-Waldhof, Fed. Rep. of Germany), issued Mar. 5, 1985. Reference should be made to said patent for its full disclosure, including the methods of preparing and using this compound. The entire disclosure of the '067 patent is incorporated herein by reference.

In accordance with the present invention, it has been unexpectedly found that a novel salt form of carvedilol, namely the methanesulfonate salt, exhibits a significantly higher aqueous solubility than the corresponding free base or other prepared salts. The aqueous solubility data for carvedilol and its salt forms determined at 25° C. are presented in Table 1.

TABLE 1

Aqueous Solubility (mg/mL) at 25° C. for Carvedilol and its Salt Forms

| Time, hr | Carvedilol (ug/mL)* | Hydrochloride | Adipate | Tartrate | Methanesulfonate |
|---|---|---|---|---|---|
| 0.5 | 5.0 | 1.65 | 0.46 | 0.71 | 8.17 |
| 1 | 9.8 | 1.63 | 0.42 | 0.70 | 8.40 |
| 4 |  | 1.37 | 0.25 | 0.56 | 8.67 |
| 24 | 11.6 |  |  |  | 8.70 |
| 70 |  | 1.06 | 0.28 | 0.68 | 11.2 |

*Note:
the solubility of carvedilol is given in micrograms per milliliter.

The data from Table 1 demonstrates that the methanesulfonate salt of carvedilol exhibits an aqueous solubility in excess of 8 mg/ml, while the hydrochloride, adipate and tartrate salt forms are poorly soluble in water. Thus, the methanesulfonate salt of carvedilol provides for the development of bioenhanced dosage forms and patient-compliant injectible dosage forms.

Carvedilol methanesulfonate salt form can be formulated in accordance with the present invention in an injectible form, an oral solid dosage form (as an immediate release or modified release [i.e. controlled release, delayed release or pulsatile release] capsule or tablet) or as a transdermal patch, in particular, in pharmaceutical compositions for the treatment of congestive heart failure, hypertension and angina.

By controlled release is meant any formulation that achieves slow release of drug over an extended period of time. In the controlled release formulations of the instant invention, a portion of the carvedilol methanesulfonate in the formulation is made available as a priming dose and the remainder is released in a sustained fashion. Examples of controlled release systems are a matrix tablet or bead formulation, and a barrier film coated tablet or bead/pellet formulation.

By delayed release is meant any formulation wherein the release of the drug is delayed for certain time or minimum under acidic conditions but rapid above a certain pH depending on the polymer used for the barrier film coat. Examples of delayed release systems include timed-release tablets and capsules and enteric-coated tablets and beads.

By pulsatile release is meant any multi-unit tablet or capsule formulation where in individual mini-tablets or particulates/pellets/beads are polymer barrier film coated, that utilizes intermittent pulsatile dosings of carvedilol methanesulfonate from one or more units as a function of time.

Such modified release formulations are preferably formulated in a manner such that release of carvedilol methanesulfonate is affected predominantly during the passage through the stomach and the small intestine to the colon.

Examples of controlled release, pulsatile release and delayed release formulations which are suitable for incorporating carvedilol methanesulfonate are described in:

Sustained Release Medications, Chemical Technology, Review No. 177, Ed. J. C. Johnson, Noyes Data Corporation (1980);

Controlled Drug Delivery, Fundamentals and Applications, 2nd Edition, Eds. J. R. Robinson, V. H. L. Lee, Mercel Dekkes Inc., New York (1987);

Remington's Pharmaceutical Sciences, 16th Edition, Ed. A. Osol, Mack Publishing Company (1980); and Solubility Considerations and Design of Controlled Release Dosage Forms, by G. M. Venkatesh, Polymer Preprint, Volume 40, pp 322, 1999 (American Chemical Society).

The process for preparing the solid dosage forms in accordance with the present invention may be carried out using a combination of a planetary mixture, a V-blender, a high shear granulator, a fluid bed granulator, a slugging press, a roller compactor, a cummunuting mill, sieving equipment, or a tableting machine. Optionally, the granulation of the hydrated or anhydrous form of carvedilol methanesulfonate, produced using a conventional dry or wet granulating equipment, is suitable for the preparation of immediate or modified release dosage forms. The preferred unit dosage forms include tablets or capsules. The compositions of this invention may be formulated by conventional methods of admixture such as blending, filling and compressing. Suitable pharmaceutically acceptable carriers for use in this invention include diluents, fillers, binders and disintegrants. An intra-venous formulation is prepared by methods known in the industry.

Immediate and modified release matrix beads may be manufactured using a extrusion-spheronization system. A wet granulated mass suitable for extrusion is prepared by blending the drug, a binder and a diluent or a matrix forming polymer, processing through a extrusion-spheronization system and collecting beads of a desired size fraction. The release profiles of the drug from these beads may further be modified by applying a barrier film coat. A buffer-based membrane-coated bead formulation may also be manufactured by a slurry-coating process as discussed in Pharmaceutical Development and Technology, Volume 3, pp 477–485 (1998). Alternately, transdermal patches for administration of carvedilol methanesulfonate through the skin at a predetermined rate can also be manufactured.

Any combination of pharmaceutically acceptable excipients, e.g. buffers, carbohydrates, diluents, fillers, binders and disintegrants, in desired proportions may be utilized in accordance with the wet or dry granulation process or direct compression formulation of the present invention. The excipients commonly used in pharmaceutical industry are well described in the literature [refer to the Handbook of Pharmaceutical Excipients, A. Wade and P. J. Weller (Editors), American Pharmaceutical Association (1994)]. Pharmaceutically acceptable fillers and diluents include, but are not limited to, the following: lactose (hydrous as well as anhydrous), starch [unmodified (corn starch) or modified (for example, Starch 1500 available from Colorcon)], sucrose, mannitol, sorbitol, cellulose, inorganic sulfates and phosphates. Disintegrants include, but are not limited to, the following: sodium starch glycolate, sodium carmellose and crosslinked polyvinyl pyrrolidone, and binders include, but are not limited to, the following: gelatin, corn starch, modified starch (Starch 1551, pregelatinized starch), hydroxypropyl methyl cellulose (HPMC), hydroxypropyl cellulose (HPC), sodium carboxy methyl cellulose, alginic acid, acacia, etc. Examples of excipients suitable for modified release applications include, but are not limited to, the following: high molecular weight HPMCs, polymethacrylate polymers known as Eudragits, polyethylene oxide, Polyox® (Union Carbide Corporation), modified ethyl cellulose, Surelease® (Colorcon), crosslinked acrylic acid polymers, Carbopol® (BF Goodrich Speciality Chemicals) and waxy materials, such as glyceryl behenate (Compritol®, glyceryl palmitostearate (Precirol®), and Gelucires® [all from Gattefosse s.a., France] and carnauba wax.

The matrix formulations of the present invention may be prepared using three types of materials: insoluble plastics, hydrophilic polymers or fatty compounds. Plastic matrices include methyl acrylate-methacrylate, polyvinyl chloride and polyethylene. Hydrophilic polymers include methylcellulose, hydroxypropylmethylcellulose (HMPC) and sodium carboxymethylcellulose. Fatty compounds include various waxes such as carnauba wax and glyceryl tristearate. The most common method of preparation is to mix carvedilol with the matrix material and then compress the mixture into tablets. In the case of wax matrices, carvedilol is generally dispersed in molten wax, which is then congealed, granulated and compressed into cores. In the matrix formulation containing carvedilol, the priming dose (the portion of the carvedilol that is immediately available in the formulation) is placed in a coat of the tablet. The coat can be applied by press coating or by conventional pan or air suspension coating.

Delayed release formulations containing carvedilol methanesulfonate may be prepared either by coating particles or granules or tablets with enteric polymers which are resistant to acids but soluble at alkaline pHs. Examples of enteric polymers are hydroxypropylmethyl cellulose phthalate, cellulose acetate phthalate or butyrate, polyvinyl acetate phthalate, Eudragit L and S polymers. Thus, the release of carvedilol methanesulfonate can be controlled by adjusting the thickness of the barrier coat and/or by a proper choice of the enteric polymer. The coated particles can be filled into capsules or optionally compressed into tablets.

The present invention also provides for various combinations of immediate release and controlled release forms. For example, the uncoated sustained release matrix core may be in combination with an immediate release form of carvedilol methanesulfonate and/or a coated matrix form. The matrix core may be comprised of a multitude of pellets coated independently with different release-delaying substances, all of which may be combined with uncoated or immediate release forms of carvedilol methanesulfonate.

The present invention provides a method of treating hypertension, angina and congestive heart failure by administering an effective amount of an immediate release or controlled release or delayed release formulation containing carvedilol methanesulfonate, or a combination thereof, for treating hypertension, angina and congestive heart failure. The formulations of the instant invention may also be used in organ protection, for example, in cardioprotection.

The following examples are illustrative of the instant invention. These examples are not intended to limit the scope of this invention as defined hereinabove and as claimed hereinbelow.

In Examples 2–5, below, the term "internal granules" means the granulation obtained by blending and granulating ingredients (drug substance and excipients) by a wet or dry granulation process.

EXAMPLES

Example 1

Preparation of carvedilol methanesulfonate: Carvedilol was suspended in an aqueous solution of methanesulfonic acid, with the acid being present at a 1:1 molar ratio. The suspension is vortexed during the addition of carvedilol powder. After storage of the suspension for 6–15 hrs, the suspension is filtered and the solid residue is dried.

Example 2

56.0 parts of carvedilol methanesulfonate, 40 parts of powdered mannitol and 4.0 parts of pregelatinized starch (Starch 1551), a binder are granulated in a planetary mixer using purified water as the granulating agent. The moist granulation is wet milled and dried using a fluid bed drier or an appropriate drying device. The dried granulation is milled to produce granules passing through a #30 mesh or appropriate size sieve. Compression mixes with ingredients as listed in Formulas 1 and 2 are prepared by blending and compressed into 30.0 mg (as carvedilol free base) tablets with a tensile strength in the range of 3–10 kP using a tablet press. Tablets of Formulas 1 and 2 disintegrate in less than 2 minutes when tested in purified water at 37° C.

| Ingredients (mg/tab) | Formula 1 | Formula 2 |
| --- | --- | --- |
| Internal granules | 68.7 | 68.7 |
| Microcrystalline cellulose | — | 7.5 |
| Crospovidone, crosslinked PVP | 3.6 | 3.0 |
| Magnesium stearate | 0.7 | 0.8 |
| Total | 73.0 | 80.0 |

Example 3

56.0 parts of carvedilol methanesulfonate, 40 parts of fumaric acid and 4.0 parts of PVP, a binder, are dry granulated using a chilsonator, a Fitzmill and sieve-shaker to produce granules passing through a #30 mesh or appropriate size sieve. Compression mixes with ingredients as listed in Formulas 3 and 4 are prepared by blending and compressed into 30.0 mg tablets of hardness in the range of 5–10 kP using a tablet press.

| Ingredients (mg/tab) | Formula 3 | Formula 4 (DC Formula) |
| --- | --- | --- |
| Carvedilol methanesulfonate |  | 38.5 |
| Internal granules | 68.7 |  |
| Microcrystalline cellulose | 20.5 | 15.5 |
| Spray dried lactose |  | 26.0 |
| Crospovidone, crosslinked PVP |  | 4.0 |
| Magnesium stearate | 0.8 | 1.0 |
| Total | 90.0 | 85.0 |

Example 4

56.0 parts of carvedilol methanesulfonate, 32.0 parts hydroxypropylmethyl cellulose (Methocel E4M, from Dow Chemical Co.), 8.0 parts of Methocel E15LV, 4.0 parts crosslinked polyvinylpyrrolidone (Crospovidone) and 4.0 parts of pregelatinized starch (Starch 1551), a binder are granulated in a planetary mixer using purified water as the granulating agent. The moist granulation is wet milled and dried using a fluid bed drier or an appropriate drying device. The dried granulation is milled to produce granules passing through a #30 mesh or appropriate size sieve. A compression mix is prepared by blending 68.7 parts of the granulation and 0.8 part of magnesium stearate and compressed into 30.0 mg tablets releasing the drug at a predesigned fashion.

Modified Release Formulations

Example 5

80.0 parts of carvedilol methanesulfonate, 5.0 parts of hydroxypropylmethyl cellulose, and 15% glyceryl behenate (Compritol) are blended, roller compacted, milled using a Fitzmill milled to produce granules passing through an appropriate size sieve. Compression mixes with ingredients as listed in Formulas 5 and 6 are prepared by blending and compressed into 30.0 mg tablets. Tablets of Formula 6 disperse rapidly in the dissolution medium or on oral administration, and the drug is released from the granules over a long period.

| Ingredients (%) | Formula 5 | Formula 6 |
| --- | --- | --- |
| Internal granules | 48.1 | 48.1 |
| Microcrystalline cellulose | 11.2 | 33.1 |
| Crospovidone, crosslinked PVP |  | 3.0 |
| Magnesium stearate | 0.7 | 0.8 |
| Total | 60.0 | 85.0 |

Example 6

Tablets of Formulas 1 and 2 are applied a membrane barrier coat using Eudragit RL polymer to provide for a long lasting release profile. Tablets of Formulas 3 and 4 are provided with an enteric coat using Eudragit L30D to produce delayed release dosage forms. A seal-coat and an over-coat are optionally applied to the tablets of these formulations.

Example 7

80 parts of carvedilol methanesulfonate, 10 parts microcrystalline cellulose and 10 parts of Povidone (PVP) are granulated, extruded and spheronized using microcrystalline cellulose for dusting. Dried beads of a desired size fraction are also coated with a Surelease formulation to provide a barrier membrane of different thicknesses. Uncoated and coated beads at desired proportions are filled into hard gelatin capsules.

Example 8

Non-pareil sugar seeds are layered with carvedilol methanesulfonate by slurry coating in a fluid bed granulator a suspension of the drug and talc in an aqueous Povidone solution. The pellets are hot melt coated with a waxy formula listed below, and cured for 12 hrs at 40° C.

| Pellet | % W/W (approx) |
|---|---|
| Non Pareil Seed | 39 |
| Carvedilol | 49 |
| Povidone | 10 |
| Talc | 2 |
| Coating | % w/w |
| Glycerylmonostearate | 37 |
| Glyceryldistearate | 53 |
| White Wax | 10 |

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is carvedilol methanesulfonate.
2. A pharmaceutical composition comprising the compound according to claim 1 and a pharmaceutically acceptable carrier.
3. A controlled release formulation comprising the compound according to claim 1 in dosage unit form.
4. A delayed release formulation comprising the compound according to claim 1 in dosage unit form.
5. A matrix formulation comprising the compound according to claim 1 in dosage unit form.
6. An enteric coated formulation comprising the compound according to claim 1 in dosage unit form.
7. A method of treating hypertension, congestive heart failure or angina which comprises administering to a subject in need thereof an effective amount of the compound according to claim 1.
8. A process for the preparation of carvedilol methanesulfonate which comprises reacting carvedilol with an aqueous solution of methanesulfonic acid, with the acid being present at a 1:1 molar ratio.

* * * * *